United States Patent [19]

Badey et al.

[11] Patent Number: 4,756,725
[45] Date of Patent: Jul. 12, 1988

[54] TRAPPING TUBE ADAPTED TO BE FITTED AT THE OUTLET OF A GAS CHROMATOGRAPH AND DEVICE FOR SUPPORTING AND PRESENTING SUCH A TUBE

[75] Inventors: Jean-Paul Badey, Saint Didier au Mont d'Or; Jean-Roger Desmurs, Saint Symphorien dOzon; Michel Dumont, Brignais, all of France

[73] Assignee: Rhone-Poulenc Recherches, Courbevoie Cedex, France

[21] Appl. No.: 900,680

[22] Filed: Aug. 27, 1986

[30] Foreign Application Priority Data

Aug. 27, 1985 [FR] France ............... 85 12912

[51] Int. Cl.⁴ ............................................. B01D 15/08
[52] U.S. Cl. ........................................ 55/197; 55/269; 55/386; 55/461; 422/99; 422/101
[58] Field of Search ............... 55/195, 197, 267, 269, 55/386, 461, 466; 73/23.1; 422/99, 101; 436/181

[56] References Cited

U.S. PATENT DOCUMENTS

| | | | |
|---|---|---|---|
| 1,877,151 | 9/1932 | Turner | 422/101 |
| 2,006,513 | 7/1935 | Rascher et al. | 422/101 |
| 2,485,739 | 10/1949 | Johnstone | 422/99 X |
| 2,659,452 | 11/1953 | Gaydasch | 55/461 X |
| 2,983,184 | 5/1961 | Ferrari, Jr. | 422/99 X |
| 3,074,982 | 1/1963 | Anderson et al. | 422/101 X |
| 3,276,265 | 10/1966 | Taft | 55/386 X |
| 3,374,607 | 3/1968 | Fisher et al. | 55/67 |
| 3,608,276 | 9/1971 | Bloomer | 55/461 X |
| 4,363,639 | 12/1982 | Gladon | 422/101 X |
| 4,559,808 | 12/1985 | Sturman | 422/101 X |
| 4,608,065 | 8/1986 | Lai | 55/461 X |

FOREIGN PATENT DOCUMENTS

| | | | |
|---|---|---|---|
| 2920876 | 11/1980 | Fed. Rep. of Germany | 422/101 |
| 1340440 | 9/1963 | France . | |
| 1557133 | 1/1969 | France . | |
| 2205203 | 5/1974 | France . | |
| 401218 | 1/1943 | Italy | 422/99 |
| 2007534 | 5/1979 | United Kingdom | 422/99 |
| 247606 | 7/1969 | U.S.S.R. | 55/386 |

*Primary Examiner*—Robert Spitzer
*Attorney, Agent, or Firm*—Burns, Doane, Swecker & Mathis

[57] ABSTRACT

This invention relates to a trapping tube characterized in that it is constituted by a shaped tube comprising:

a first section or zone of condensation of the separated gaseous phase delivered by the outlet of the chromatograph, a second section or zone of confinement of the condensate of the separated gaseous phase, and a third section or zone of evacuation of the vector gas of the separated gaseous phase. The invention is more particularly applicable to the obtaining of condensates in a small, even infinite quantity.

17 Claims, 3 Drawing Sheets

U.S. Patent    Jul. 12, 1988    Sheet 1 of 3    4,756,725
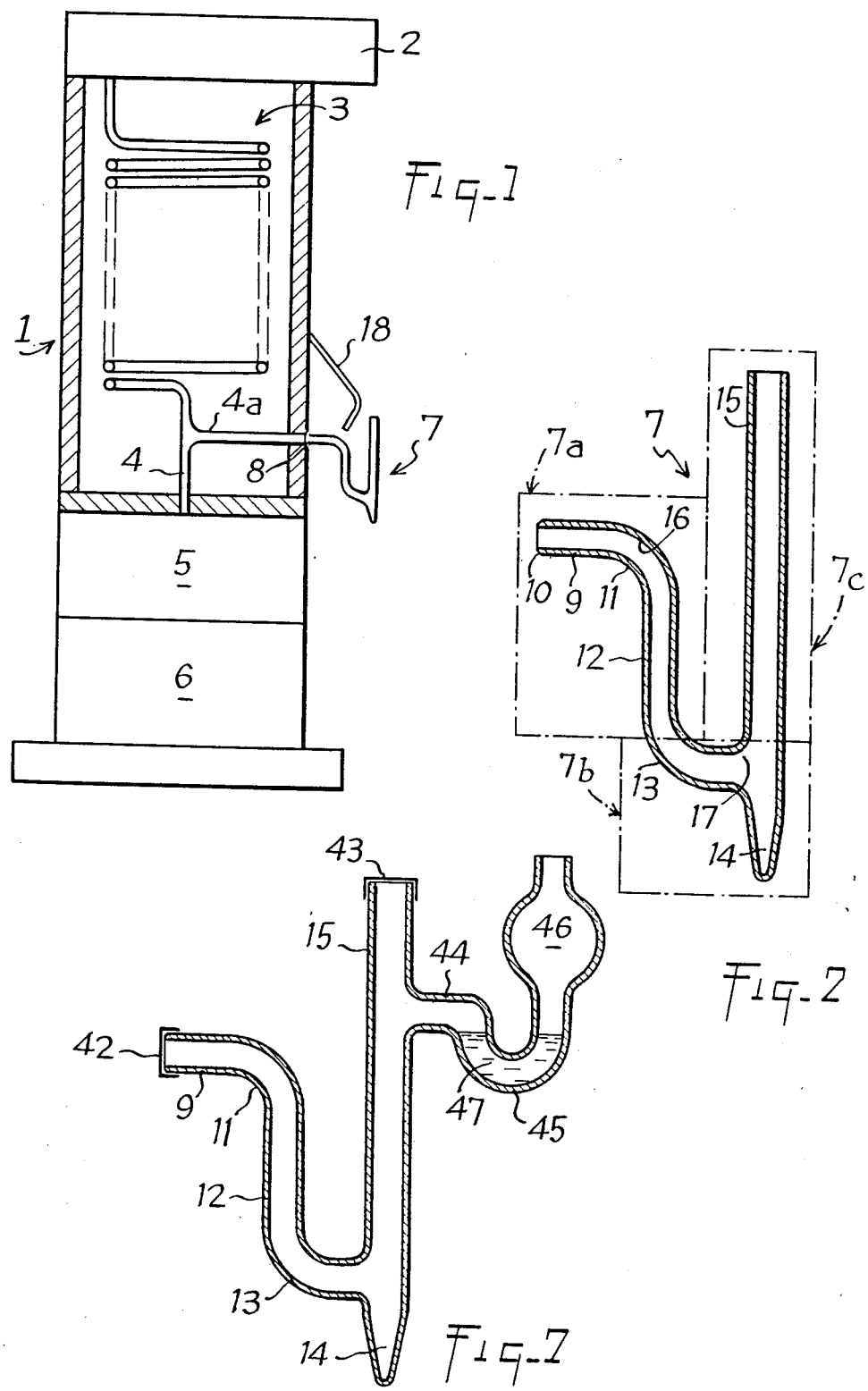

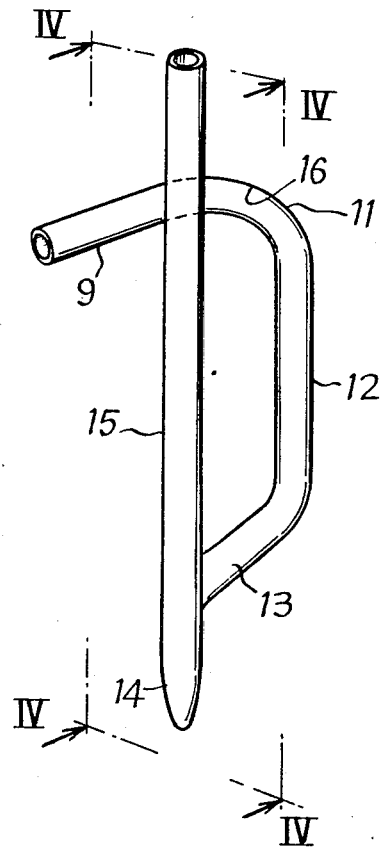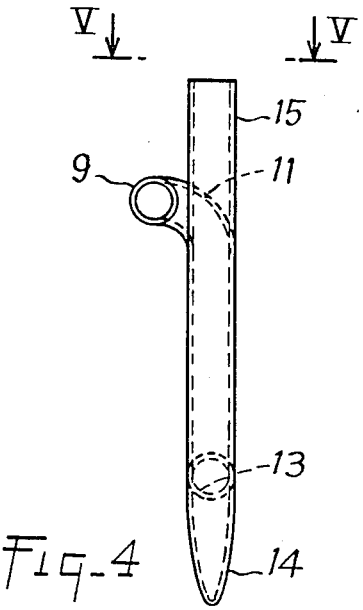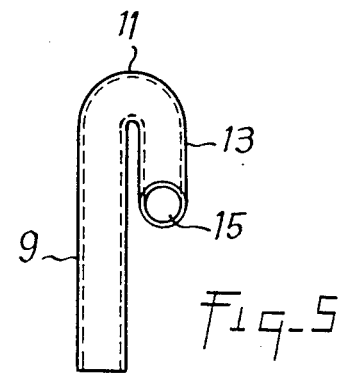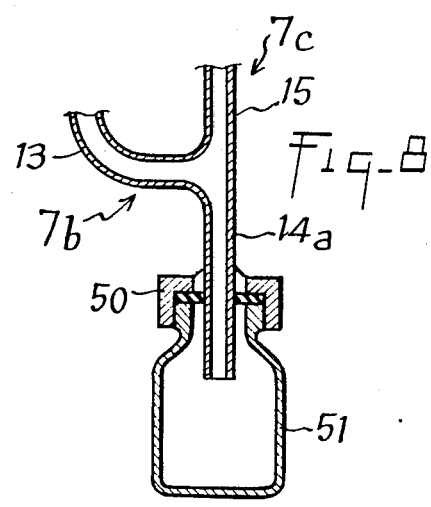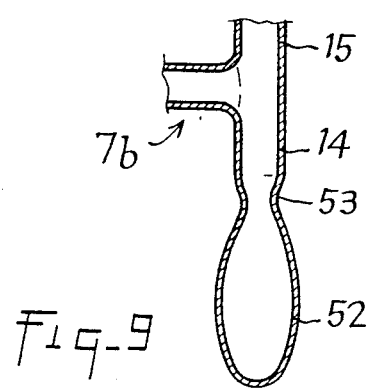

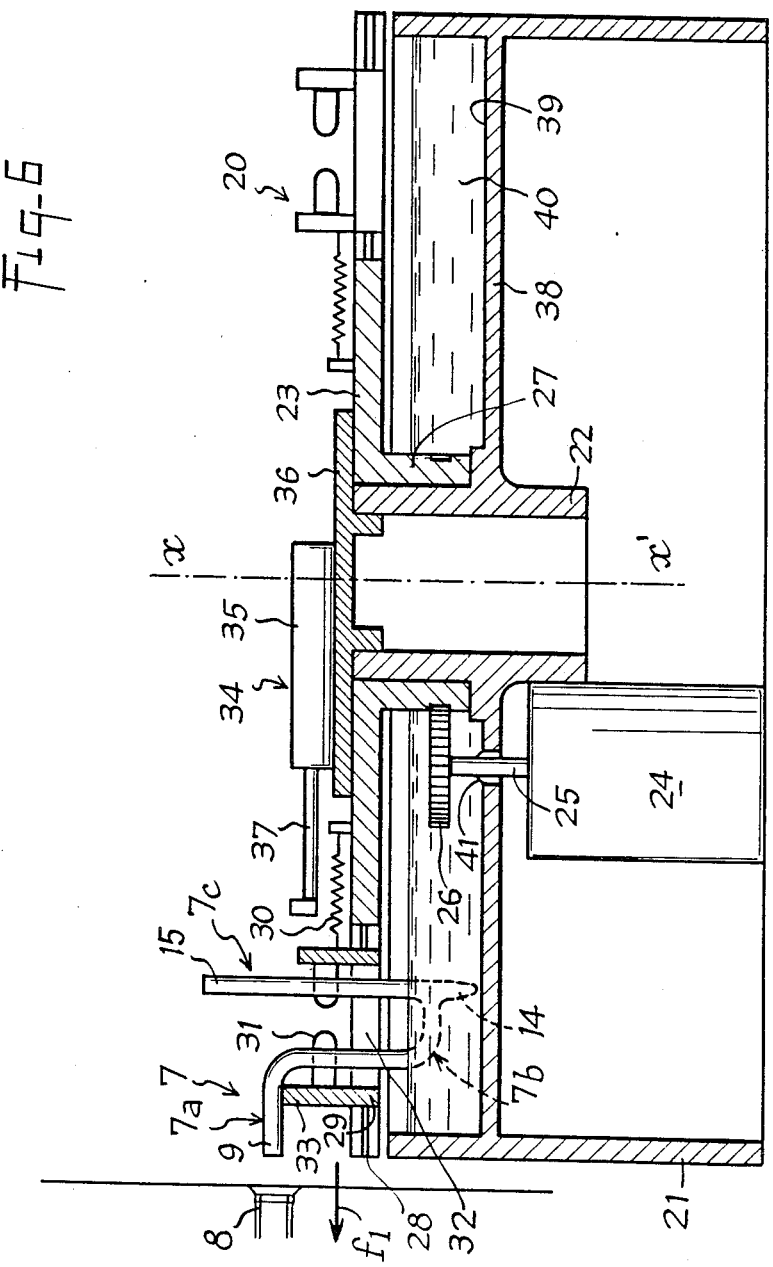

TRAPPING TUBE ADAPTED TO BE FITTED AT THE OUTLET OF A GAS CHROMATOGRAPH AND DEVICE FOR SUPPORTING AND PRESENTING SUCH A TUBE

BACKGROUND AND OBJECTS OF THE INVENTION

The present invention relates to the technical domains of analysis of products by gas-chromatography.

The principle of gas chromatography is based on the separation of at least two different compounds coming within the composition of a product, in a chromatography column where levels of balance and of separation are established on a porous substrate included in the column.

The apparatus for carrying out such a principle comprise an injector of the product having to be analyzed, a chromatography column placed in an oven with adjustable temperature, a detector of the gaseous phases successively separated and corresponding to the different components of the product and a recorder coupled with the detector.

Apparatus of the above type are satisfactory and enable a chromatogram to be obtained which corresponds to the different vapour phases successively separated.

However, very often, such chromatograms can be validly interpreted in practice only insofar as it is possible to identify the peaks of the chromatogram in relation with the separated vapour phases.

There is therefore a need to be able to withdraw at the outlet of a chromatograph, at least partially, the successively separated vapour phases, so as to be able to proceed on these phases with analyses of identification in order to determine the structure thereof.

The technique heretofore recommended to this end is generally called preparative gas-chromatography and consists in collecting at the outlet of the chromatograph, at least part of each separated gaseous phase.

Preparative gas-chromatography includes a trapping phase consisting in collecting all or part of a separated vapour phase in order to have available, after condensation, a pure standard substance for reference or identification during subsequent analysis work.

For the trapping technique to respond to these objectives, it must be able to furnish products of high purity, capable of being recovered even in a small quantity, being given that it is more and more necessary to work on small samples, due to the cost of the reagents and of the products having to be analyzed, their toxicity or the necessity of short response times which can generally be attained only by means of small-section chromatography columns enabling the finest resolutions to be obtained.

Such a technique must also be able to ensure a certain non-polluted confinement of a small, even minute, quantity of recovered condensate, whilst allowing easy recovery thereof.

Such a technique must also furnish a good trapping yield, in order to limit the successive operations of separation, when the vapour phase to be separated enters in a very small proportion in a product to be analyzed which is available only in a small quantity.

In order to carry out such a trapping technique satisfactorily, it is consequently important to be able to ensure, under optimum conditions and as quickly as possible, the withdrawal of all or part of a separated gaseous phase delivered by the outlet of the chromatograph, and to ensure condensation thereof under good conditions, without risk of pollution.

To carry out such a technique, the prior art proposes several methods.

The first consists in placing, by hand, at the outlet of the chromatograph, a tapered straight tube open at the two ends to recover the separated vapour phase.

This technique is not precise and does not allow a suitable confinement with a good yield, due to the shape of the tube.

To improve this technique, the prior art has also recommended to mount on the outlet of a chromatograph, a valve with multiple outlets which are each connected by a pipe to a recovery tube, most often subjected to a forced cooling by an installation which is always cumbersome and sometimes complex. The valve is controlled in relation with the chromatogram, so as to direct each successively separated vapour phase towards a different recovery tube.

However, this technique, although clearly preferable to the preceding one, presents numerous drawbacks.

The imperative tightness which the valve must present cannot be obtained for certain over a period of time, due, mainly, to the expansions which are imposed thereon by the relatively high temperature of the separated vapour phases delivered by the chromatograph.

These problems of tightness are frequently the cause of pollutions of the separated vapour phases by the ambient medium. The obtaining of condensates of high purity and in small quantity is therefore random.

An additional factor of pollution resides in the fact that a fraction of the previously separated vapour phase distributed always remains in the valve body and that this residual fraction consequently constitutes a source of pollution for the following separated vapour phase.

Another source of pollution resides in the fact that the control of the valve induces, within the column of the chromatograph, successive variations in pressure which disturb the operation of the latter, to the point of altering the capacities of separation or of resolution.

Another drawback of this technique comes from the fact that it would be necessary to construct the valve in a material which is inert with respect to a large number of products in order to avoid any risk of oxidation or corrosion in time.

In an attempt to overcome certain of the drawbacks of the above technique, it has been proposed to eliminate the single distribution valve for all the circuits leading to the recovery tubes and to allocate one valve to each of them. In such a case, the different recovery circuits are connected at a common point to the outlet of the chromatograph.

Such a technique may be of interest as it eliminates the risks of pollution by the residual fractions remaining inside the single valve. However, the same other drawbacks as those set forth hereinabove must be imputed to such a trapping installation.

In an attempt to solve the problem raised, the prior art further proposes another method consisting in fitting a hollow needle at the outlet of a chromatograph, for example in relation with the detector. This needle is made to pass through a vented septum obturating a recovery tube subjected to cooling to ensure condensation of the separated gaseous phase which it is adapted to receive.

This method presents a certain number of appreciable drawbacks.

Firstly, the hollow needle is directed downwardly, in an orientation favourable to pierce the septum of each tube. Such an orientation is not favourable to the recovery of a gaseous phase.

In all cases, the needle is disposed in the ambient medium, i.e. most often in the open air, without being heated. The circulation of a gaseous phase may then produce, particularly for the heaviest compounds, an internal condensation leaving traces which pollute the gaseous phase subsequently separated.

Furthermore, the tubes equipped with the vented septum generally comprise one or more internal baffles provided to facilitate the condensation of the separated gaseous phase. The presence of these baffles represents an obstacle which is sometimes insurmountable for the direct withdrawal of the condensate.

The prior art techniques recommended are therefore not able to respond positively to the objectives having to be taken into account and which are:

the possibility of confinement of the condensates, even in a very small quantity, the absence of pollution of the trapped condensates, the possibility of easy withdrawal of the condensate, even obtained in a small quantity, the obtaining of a good trapping yield, the absence of a complex, expensive and delicate installation to ensure cooling of each separated gaseous phase.

It is precisely an object of the invention to propose a novel trapping tube, adapted to be fitted to the outlet of a gas chromatograph and of which the design responds to the objects set forth hereinabove, employing only a simple structure easy to produce, of low cost and adapted to be rendered automatic.

To attain this objective, the trapping tube according to the invention is characterized in that it is constituted by a shaped tube comprising:

a first section or zone of condensation of the separated gaseous phase delivered by the outlet of the chromatograph, a second section or zone of confinement of the condensate of the separated gaseous phase, and a third section or zone of evacuation of the vector gas of the separated gaseous phase.

It is a further object of the invention also to propose, for the support and presentation of trapping tubes, a device for manual, semi-automatic or totally automatic operation then synchronized with the operation of the phase detector associated with a gas chromagraph.

Such a device for supporting and presenting trapping tubes is characterized in that it comprises:

a fixed support, a mobile plate mounted on the support, a motor member for driving the plate step by step in front of the outlet of the chromatograph, n carriages for supporting and presenting n trapping tubes each mounted on the plate via a slideway extending parallel to the axis of the outlet when the corresponding carriage is in position of presentation, means for controlling, on the one hand, the individual displacement of each carriage placed in position of presentation, in the direction of the outlet of the chromatograph to ensure placing of the tube and outlet into relationship and, on the other hand, the automatic return of said carriage into standby position.

THE DRAWINGS

The invention will be more readily understood on reading the following description with reference to the accompanying drawings, in which:

FIG. 1 is a schematic view, partly in section, illustrating a gas chromatograph equipped with a trapping tube according to the invention.

FIG. 2 is an elevational section illustrating, on a larger scale, the shape of the trapping tube according to the invention.

FIG. 3 is a perspective view illustrating, on a different scale, a variant embodiment of the tube according to the invention.

FIG. 4 is a lateral view taken substantially along plane IV—IV of FIG. 3.

FIG. 5 is a plan view taken along line V—V of FIG. 4.

FIG. 6 is a schematic elevational section of a device for supporting and presenting the trapping tube according to the invention.

FIG. 7 is an elevational section showing another embodiment of the object of the invention.

FIGS. 8 and 9 are two partial elevational sections showing two other variant embodiments of the tube according to the invention.

DETAILED DESCRIPTION OF PREFERRED EMBODIMENTS OF THE INVENTION

Referring now to the drawings, FIG. 1 schematically shows a gas-chromatograph generally designated by reference 1. Such a chromatograph 1 comprises in known manner an injector 2 adapted to receive the quantity of the product having to be subjected to the separation, by chromatography, of its different components. The injector 2 is connected to a chromatography column 3 of which the outlet 4 terminates in a detector 5, most often coupled to a recorder 6. The trapping tube, generally designated by reference 7, is adapted to be placed in relationship with an outlet tube 4a which may be connected in by-pass to the inlet or to the outlet of the detector 5. To that end, the tube 4a comprises a terminal part 8 generally shaped as an endpiece or adaptation connector of geometrical configuration, in the form of truncated bearing surface or the like most often retaining a seal of the O-ring type.

The trapping tube 7 according to the invention is constituted by a shaped tube made, preferably but not exclusively, of blown glass. The shape given to tube 7 is such as to provide it with a first section 7a, called zone of condensation of a separated gaseous phase, delivered by the outlet 8 of the chromatograph 1. This first section 7a comprises a rectilinear inlet pipe 9 of circular section and comprising a transverse edge 10, preferably convex. The pipe 9 is extended by a condensation bend 11, for example covering an angular amplitude equal to 90° and extended by a rectilinear trickling column 12.

In the embodiment illustrated, the zone of condensation 7a is formed so that the pipe 9 extends substantially horizontally and the column 12 is oriented downwardly, in a substantially vertical direction to be connected to a second section 7b, hereinafter called zone of confinement of the condensate of the separated gaseous phase.

Zone 7b comprises a flow bend 13 following the column 12 and terminating in an appendix 14 with closed bottom extending downwardly and constituting a storage cavity or reservoir.

According to the structure shown in FIG. 2, bend 13 covers an angular range substantially equal to 90° and is placed in the plane common to pipe 9, bend 11 and column 12, as well, moreover, as appendix 14. FIG. 2 shows that appendix 14 is preferably tapered downwardly to present a useful section reducing progressively. However, a different shape may be retained.

The trapping tube 7 comprises a third section 7c hereinafter called zone of evacuation of the vector gas. This third section comprises a shaft 15 extending vertically upwardly, from bend 13 and substantially, if not exactly, in line with appendix 14. Shaft 15 is placed in the same plane as appendix 14 and as first section 7a and its upper end is open.

The use of the trapping tube described hereinabove consists in placing the pipe 9 in relation with the outlet endpiece 8, so that the O-ring of the latter cooperates with the outer peripheral surface of the pipe 9 and establishes a tight interpenetration connection in order to avoid any communication between the outlet tube 4a and the ambient medium.

The trapping tube 7 is maintained by any suitable means in this position, by being placed so that the plane of the trickling column 12 is directed vertically and the appendix 14 then constitutes the bottom point of the trapping tube.

A gaseous phase, separated by the chromatography column 3 and delivered by the outlet tube 4a, thus necessarily follows the pipe 9 which directs it towards the condensation bend 11. The speed of circulation and the impact that the molecules undergo on the inner surface of bend 11, more particularly localized at 16, as well as the difference in temperature presented by this wall part maintained at the temperature of the ambient medium, promote the condensation of the molecules which are thus separated from the vector gas conveying them.

The condensed droplets, trickling along column 12, are received by bend 13 which ensures flow thereof into appendix 14 where the trapped condensate resulting from the recovery of all the droplets is progressively formed. The vector gas of the separated gaseous phase follows the same path and is naturally evacuated, following shaft 15 beyond which its nature, generally neutral or inert, allows it to disperse in the ambient medium.

The flow bend 13 ensures a complete recovery of the condensed droplets which follow the zone 17 of connection with shaft 15 to be collected in appendix 14 constituting the volume of confinement of the condensate.

It must be noted that, depending on the importance or quantity of the condensate recovered, the function of confinement may also be complementarily performed by a part of the volume of bend 13.

The trapping tube 7 may then be extracted from the outlet endpiece 8, so as to allow the subsequent use of the condensate. This use may be envisaged by acting by withdrawal, directly from the appendix 14, particularly by means of a needle adapted to the end of a suction syringe and engaged from the open end of the shaft 15 which then constitutes access for withdrawal. The needle may plunge to the bottom of appendix 14 and allow the withdrawal and recovery of the condensate, even if the latter exists only in a small, if not minute, quantity. In fact, the shape of shaft 15 and its at least partial alignment with appendix 14 enable the withdrawal needle to arrive exactly at the bottom of the appendix and to withdraw, if necessary, the whole of a minute quantity of condensate recovered.

Withdrawal may be effected directly or by providing to introduce a solvent via pipe 9. In that case, the solvent may also perform a function of rinsing, enabling the non-collected droplets still adhering to the wall of bend 11 and column 12, to be recovered.

The particular shape of the condensation section 7a is selected so as to allow, if necessary, a forced cooling in order to improve condensation of the separated gaseous phase. In fact, FIG. 1 shows that the bend 11 of the first section 7a offers a convex surface favourable for receiving a jet of cooling fluid delivered, for example, by a nozzle 18 which may be independent or borne by chromatograph 1. This cooling during the trapping phase eliminates the risk of pollution since tube 7 is then under pressure.

The structure of the trapping tube, making available three sections with separate functions which are at least partly locally independent of one another, precisely makes it possible to employ, locally, a forced cooling means promoting a rapid condensation, directly on the surface of impact encountered by the separated gaseous phase included with the vector gas, i.e. in the zone most favourable for the formation of condensation droplets.

It is indicated in the foregoing that the embodiment of FIG. 2 corresponds to a structure in which pipe 9, bend 11, column 12, bend 13 and shaft 15 are located in a common plane.

It must be considered that, in certain cases, it might be envisaged to give section 7a its own plane which would occupy an angle of inclination in one direction or in the other with respect to the plane common to bend 13 and to shaft 15. Similarly, it must be considered that shaft 15 might extend in a certain ascending inclination in a direction identical to or opposite that of an inclination which may also be given to the trickling column 12.

FIGS. 3 to 5 illustrate a variant embodiment in which bend 11 is reversed with respect to the embodiment of FIG. 2. This bend 11 is in addition partially curved, at least locally, so as to allow the reverse orientation of pipe 9 which then extends parallel to the plane containing bend 13, appendix 14 and shaft 15. This embodiment may be chosen for the condensation droplets to follow a continuous internal path from the inner zone 16 along column 12 and then to follow the internal surface of bend 13 to arrive directly in appendix 14. Such an embodiment may, in certain cases, be considered as more favourable to the formation of droplets, to their enlargement and to the establishment of a stream or jet of liquid following, without interruption of continuity, a continuous trickling and flow wall to reach appendix 14. This embodiment may be envisaged in order to avoid any risk of loss of condensate resulting from the possible entrainment of part of the condensate located in zone 17.

Trapping tubes 7 may advantageously be used, in relation with a chromatograph 1, to ensure trapping of the gaseous phases successively separated and delivered by the outlet tube 4a. FIG. 6 shows a supporting and presentation device 20 to this end. Device 20 comprises a base 21 forming a cylindrical bearing surface 22 of vertical axis, ensuring support and centering of a mobile plate 23. In the embodiment, the device 20 is of the carrousel type and comprises a circular mobile plate 23 which may be animated by a rotation on axis x–x' of bearing surface 22, by means of a motor 24 of the step-by-step type, borne by the base 21. In such a case, the output shaft 25 bears for example a driving pinion 26 adapted to cooperate with a circular toothing presented by a bearing 27 formed by the plate 23 to surround bearing surface 22 concentrically.

Plate 23 presents slideways 28 of radial direction, preferably equidistant angularly and of which the pitch constitutes the supply reference of the step-by-step motor 24. Each slideway 28 supports a carriage 29 free to slide in a reciprocating rectilinear movement in slideway 28. Each carriage 29 is associated with an elastic return member 30 allocating thereto a stable rest position by imposing thereon a constant traction stress, of centripetal direction.

Each carriage 29 presents means 31 for supporting a trapping tube 7 disposed vertically, preferably so that its plane, passing through shaft 15 and column 12, is established vertically. The means 31 may advantageously be constituted by elastic clips with deformable arms, located opposite one another above a slot 32 allowing the through engagement of at least section 7b of tube 7 through carriage 29. The vertical immobilization of each trapping tube may be established in several possible ways and, in particular, by providing each carriage 29 with a stop 33 against which pipe 9 abuts for example.

The device 20 further comprises means 34 for controlling the individual displacement of each carriage 29 in a centrifugal direction. These means 34 comprise, for example, a pneumatic jack 35 borne thereby by a platform 36 adapted to the cylindrical bearing surface 22 to extend above the plate 23. The jack 35 is oriented so that its piston rod 37 corresponds, in a position of indexation of plate 23 by motor 24, to a radial direction parallel to the axis of the outlet endpiece 8 of the chromatograph 1.

In this way, in the position shown in FIG. 6, the supply of jack 35 controls the extension stroke of rod 37 which pushes carriage 29 into horizontal rectilinear displacement in the direction of arrow $f_1$ along slideway 28. The displacement is imposed on the carriage over a length such that the pipe 9 is brought into tight interconnection relationship with the outlet endpiece 8 allowing trapping of the separated gaseous phase delivered, as described hereinabove.

After recovery, the supply of jack 35 is reversed or interrupted so as to control the retraction stroke of the rod 37 and to allow return into original stable position of carriage 29 by action of spring 30.

It thus becomes possible, by suitably programming the supply cycle of the motor 24, for example in synchronism with the operation of the detector 5 and/or recorder 6, to place in relation with the outlet endpiece 8, successively, empty trapping tubes for recovering each of the separated gaseous phases delivered by the chromatograph 1.

FIG. 6 shows that it may be advantageous to provide the base 21 with an elevated bottom 38 extending, however, in a horizontal plane lower than the upper edge of the peripheral wall of the base. This structure makes it possible to define a tank 39 containing a cooling bath 40 of which the level is determined so that at least section 7b of each tube supported is permanently immersed therein. By this means, it thus becomes possible to promote or maintain condensation, within each tube, of the separated gaseous phase or of the trapped condensate.

In such a case, the output shaft 25 of the motor 24 passes through the bottom 38 via an annular gasket 41.

The device 20 may comprise a plate animated by a rectilinear displacement perpendicularly to the axis of the endpiece 8 and which would bear n carriages adapted to be displaced individually in a direction parallel to the axis of said endpiece.

In certain cases and in particular in the one described hereinabove consisting in subjecting section 7c of each tube to a pre-cooling, it may be useful, and even necessary or imperative, to avoid any pollution of the inner volume of the tube, particularly by the condensation of the water vapour of the ambient medium.

To avoid such pollution, it may be provided to make the trapping tube as illustrated in FIG. 7. The end of pipe 9 and that of shaft 15 are obturated by two septums 42 and 43 adapted to be pierced, respectively, by a hollow needle with which the outlet endpiece 8 is fitted, and by the withdrawal needle fitted on the end of the syringe.

To facilitate in such a case the evacuation of the vector gas, it is then possible to provide shaft 15 with a branch conduit 44 forming a siphon 45 and terminating or opening in the free air by a bulb 46. Siphon 45 is advantageously occupied by a liquid medium 47, such as mercury or oil, in order to constitute a hydraulic obturator opposing the placing into relationship of the inner volume of the tube and the ambient medium, whilst allowing, during use, the escape of the vector gas in such a medium. In such a case, the bulb 46 constitutes an expansion vessel opposing the possible projections of the liquid medium 47.

The branch conduit 44 may be fitted with an obturator of any other type performing the same function, for example with a controlled valve.

FIG. 8 shows a variant embodiment consisting in providing the second section or zone of confinement 7b with a separable cavity or reservoir. In this embodiment, part 7b comprises an open-bottom appendix 14a provided to be engaged in and maintained with tightness by the removable cover 50 of a recipient 51 in which the appendix 14a is immersed.

FIG. 9 shows another embodiment of a separable reservoir. In this example, section 7b comprises an appendix 14 forming at its end a bulb 52 preferably extending beyond a contraction or necking 53. It thus becomes possible, after recovery of the condensate, to separate and seal the bulb 52 which represents, once detached from tube 7, a clean packaging for the condensate, facilitating transfer or momentary storage thereof.

The trapping tube according to the invention presents a shape giving it a good mechanical strength and remarkable trapping characteristics following from the good condensation of the products, even the most volatile ones, the absence of pollution of the condensates and the easy recovery of these condensates even in a small quantity.

By employing such a tube and device 20, precise, pure samples may automatically be collected, even in a small or minute quantity, without the permanent presence of qualified personnel having to ensure constant surveillance or intervention.

The invention is not limited to the examples described and shown, as various modifications may be made thereto without departing from its scope.

What is claimed is:

1. A trapping tube adapted to be fitted at the outlet of a gas-chromatograph wherein it is constituted by a shaped tube comprising:

a first section or zone of condensation of a separated gaseous phase delivered by the outlet of the chromatograph, said first section having a gas inlet and a downwardly extending trickling column, a second section or zone of confinement of the condensate of the separated gaseous phase disposed downstream of said condensation zone with reference to the direction of gas flow, said zone of confinement extending below the zone of condensation and having a downwardly extending closed appendix for confining condensate, and a third section or zone of evacuation of the vector gas of the separated gaseous phase extending upwardly from said zone of confinement.

2. The trapping tube of claim 1, wherein said first section or zone of condensation comprises:
an inlet pipe at least part of which extends horizontally,
a condensation bend following the inlet pipe, and
a trickling column extending downwardly from the condensation bend,
said second section or zone of confinement comprising:
a flow bend following the trickling column, and
a storage cavity or reservoir located below the flow bend and defined by said downwardly extending appendix.

3. The trapping tube of claim 2, wherein the axes of the inlet pipe and the trickling column are located in the same vertical plane.

4. The trapping tube of claim 2, wherein the axes of the outlet pipe and of the trickling column are offset.

5. The trapping tube of claim 4, wherein the appendix has a closed bottom.

6. The trapping tube of claim 5, wherein the separable reservoir is constituted by a bulb, the inlet of which is of reduced cross-section.

7. The trapping tube of claim 4, wherein the appendix comprises a separable cavity or reservoir.

8. The trapping tube of claim 2, wherein the third section or zone of evacuation comprises a shaft rising from the flow bend and at least partly in line with the axis of the appendix.

9. The trapping tube of claim 8, wherein the axes of the shaft, the trickling column and the inlet pipe are located in the same plane.

10. The trapping tube of claim 8, wherein the third section comprises a shaft associated with an obturator.

11. The trapping tube of claim 10, wherein the obturator is of the hydraulic type and is placed on a branch conduit of the shaft.

12. The trapping tube of claim 8, wherein the inlet section of the pipe and the oulet section of the shaft are obturated by membranes.

13. Apparatus for positioning trapping tubes at the outlet of a gas chromatograph, said apparatus comprising:
a fixed support,
a mobile plate mounted on the support,
a motor member for driving the plate step by step in front of the outlet of the chromatograph,
a plurality of carriages for supporting a corresponding plurality of slideway trapping tubes, each carriage being slidably mounted on the plate for sliding movement parallel to the axis of the outlet when the corresponding carriage is disposed opposite said outlet, and
means for extending said carriages from a rest position toward said chromatograph outlet to bring said tubes and outlet into communication, and for returning said carriages to said rest position.

14. The device of claim 13, wherein each carriage comprises a through slot in which the trapping tube is engaged, a part of said tube immersed in a cooling bath contained by the fixed support.

15. The device of claim 14, wherein each carriage comprises a vertical engagement stop cooperating with the inlet pipe of the first section of the trapping tube.

16. The device of claim 15, wherein the carriages orient the planes of the tubes vertically.

17. The device of claim 16, wherein the means for displacing said carriages comprises a jack successively engaging with each carriage, and an elastic return member connected to each carriage for returning said carriage to its rest position.

* * * * *